(12) United States Patent
Rath et al.

(10) Patent No.: US 7,034,012 B2
(45) Date of Patent: Apr. 25, 2006

(54) COMPOSITION AND METHOD FOR PREVENTION AND TREATMENT OF ARRHYTHMIAS

(76) Inventors: Matthias Rath, 4699 Old Ironsides Rd. Ste. 300, Santa Clara, CA (US) 95054; Aleksandra Niedzwiecki, 4699 Old Ironsides Rd. Ste. 300, Santa Clara, CA (US) 95054

( * ) Notice: Subject to any disclaimer, the term of this patent is extended or adjusted under 35 U.S.C. 154(b) by 162 days.

(21) Appl. No.: 10/286,684

(22) Filed: Nov. 1, 2002

(65) Prior Publication Data

US 2005/0009904 A1   Jan. 13, 2005

(51) Int. Cl.
| | |
|---|---|
| *A61K 31/07* | (2006.01) |
| *A61K 31/34* | (2006.01) |
| *A61K 31/51* | (2006.01) |
| *A61K 31/59* | (2006.01) |
| *A61K 31/70* | (2006.01) |

(52) U.S. Cl. .................. 514/52; 514/167; 514/251; 514/276; 514/458; 514/474; 514/725; 424/602; 424/630; 424/639; 424/641; 424/646; 424/655; 424/736

(58) Field of Classification Search ............ 514/474, 514/458, 167, 251, 276, 725; 424/52, 736, 424/602, 630, 639, 641, 646, 655

See application file for complete search history.

(56) References Cited

U.S. PATENT DOCUMENTS 6,048,846 A * 4/2000 Cochran ............ 514/168

OTHER PUBLICATIONS

Spooner et al., "Sudden Cardiac Death, Genes and Arrhythmogenesis: Consideration of New Population and Mechanistic Approaches from National Heart, Lung and Blood Institute Workshop, Part I", Circulation, 2001;103:2361-2364.*
Giuliani et al., Mayo Clinic Practice of Cardiology (Third Edition), Mosby, 1996: pp. 738 and 749.*
Jacob, Leonard S. Pharmacology (The National Medical Series for Independent Study), Fourth Edition. Williams & Wilkins, 1996. pp. 3-4.*
Cardiac Arrhythmias. The Merck Manual of Diagnosis and Therapy. Merck Research Laboratories, 1992: pp. 465-473.*
Physicians Desk Reference, 2001. Medical Economics Company, Inc. p. 132.*
Rath et al. "Nutritional Supplement Program Halts Progression of Early Coronary Atherosclerosis Documented by Ultrafast Computed Tomography", Journal of Applied Nutrition, vol. 48, No. 3, 1996: 67-78.*
Goldman et al. (Editors). Cecil's Textbook of Medicine (Twenty First Edition, vol. 1). W.B.Saunders Company, 2000. p. 226-230.*

* cited by examiner

*Primary Examiner*—Christopher S. F. Low
*Assistant Examiner*—Leslie A. Royds
(74) *Attorney, Agent, or Firm*—Ali Kamarei, Esq.

(57) ABSTRACT

A composition of biochemical substances for the treatment of arrhythmia in a human susceptible to arrhythmia, and its method of administration, comprising at least one ascorbate compound selected from the group consisting of ascorbic acid, pharmaceutically acceptable ascorbate salts and/or mixtures thereof in combination with at least one carnitine compound selected from the group of carnitine hydrochloride, pharmaceutically acceptable carnitine salts and/or mixtures thereof.

4 Claims, 2 Drawing Sheets

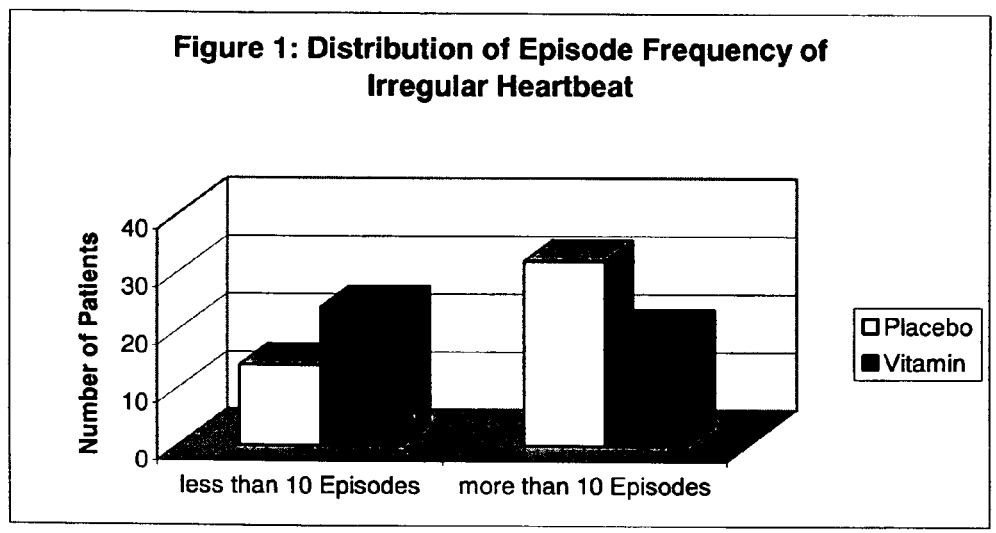

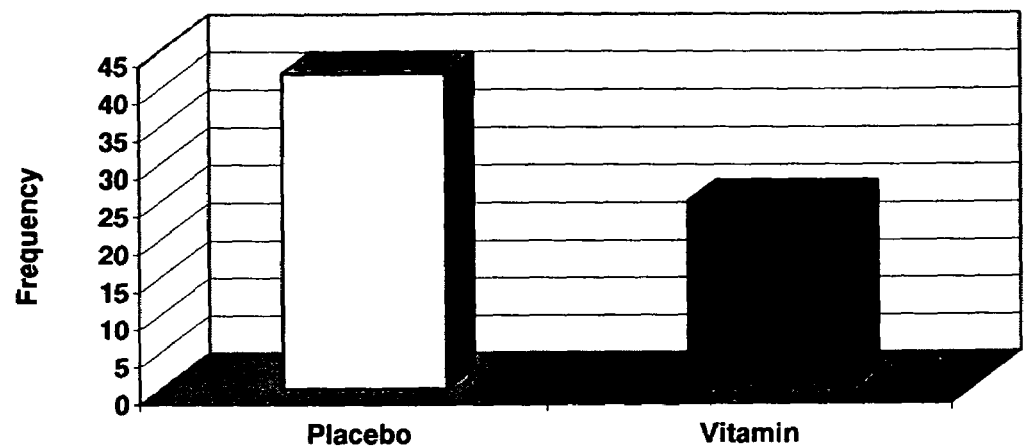

US 7,034,012 B2

COMPOSITION AND METHOD FOR PREVENTION AND TREATMENT OF ARRHYTHMIAS

FIELD

The present invention generally relates to the prevention and treatment of irregular heart beat (arrhythmias) by replenishing micronutrients as cellular biocatalysts and coenzymes of myocytes responsible for the electrical impulse generation and conduction.

BACKGROUND

The cause of many diseases in the human cardiovascular arena remains unknown. Much of what is referred to diseases is in fact the symptoms of underlying cellular diseases. For example, what is referred to the disease of hypertension is only the symptom of an elevated blood pressure, which can be caused by many different pathologies, such as vasoconstriction or high cardiac output. Much of the focus of current therapies in medicine is directed to treatment of symptoms rather than the underlying cellular malfunctions. Some of the previous work of the current inventor with regard to cardiovascular disease is contained U.S. Pat. No. 5,650,418 to Rath, et al.

Among some of the most common diseases with unknown origins is irregular heart beat or arrhythmia. This is the case for both arrhythmias originating in the atrial region of the heart (atrial arrhythmias) as well as in the ventricular region. The latest edition of the leading textbook in cardiology, E. Braunwald's "The Heart" states that the etiology of arrhythmias remain unknown. It has been speculated that disturbances in the sodium and potassium channels of myocytes plays a role in arrhytmogenesis.

Since the underlying cellular causes of arrhythmias are largely unknown, pharmacological therapies remain unspecific. Current therapies include Beta blockers, Calcium antagosists, and other specific anti arrhythmic drugs. The goal of most of these treatments is directed towards prolonging the electrical conductivity of the heart cells that are responsible for the autonomous generation of a heart beat, in order to prevent irregularities in heart beat. Current treatments, in turn, are inevitably associated with the difficulty to titrate a proper therapeutic dosage of anti-arrhythmic drugs, resulting in abnormally extended electrical conduction time and pro-arrhytmogenic side-effects with well-known complications such as sudden death.

Worldwide over one hundred million people suffer from different forms of arrhythmias, and deaths occurred as a result of taking the currently available arrhythmia drugs reaches the tens of thousands. Arrythmias can lead to sudden death caused by an arrest of the cardiac muscle, which leads to a sudden stop in blood flow. Unlike other heart attacks caused by coronary heart disease and cholesterol occluded arteries, where emergency treatment has a reasonable chance of saving the patient from death, heart attacks caused by arrhythmia are seldom survived. Furthermore, while coronary heart diseases such as atherosclorosis is seen in older humans, arrhythmias also occur in younger as well as older humans.

Thus there is an urgent need for a specific therapeutic approach to arrhythmias that is an alternative to current therapies.

There is also a need for a therapy for arrhythmia that is without the side effects generally associated with the conventional therapies currently available.

SUMMARY

The described invention provides a composition of biochemical substances for the treatment of arrhythmia in a human susceptible to arrhythmia, and its method of administration, comprising at least one ascorbate compound selected from the group consisting of ascorbic acid, pharmaceutically acceptable ascorbate salts and/or mixtures thereof in combination with at least one carnitine compound selected from the group of carnitine hydrochloride, pharmaceutically acceptable carnitine salts and/or mixtures thereof. The daily dose of the ascorbate compound is between about 75 and 26,000 mg. The daily dose of the carnitine compound is between about 10 and 4,000 mg.

In a preferred embodiment, the composition further comprises at least one taurine compound selected from the group of taurine hydrochloride, pharmaceutically acceptable taurine salts and/or mixtures thereof. The daily dose of the taurine compound is between about 10 and 4,000 mg.

In another preferred embodiment, the composition further comprises at least one magnesium compound selected from magnesium or pharmaceutically acceptable magnesium salts and/or mixtures thereof. The daily dose of the magnesium compound is between about 2 and 800 mg.

In another preferred embodiment, the composition further comprises coenzyme Q-10 (ubiquinone). The daily dose of coenzyme Q-10 is between about 2 and 600 mg.

In another preferred embodiment, the composition further comprises Vitamin B1. The daily does of Vitamin B1 is between about 2 and 400 mg. In another preferred embodiment, the composition further comprises Vitamin B2. The daily does of Vitamin B2 is between about 2 and 400 mg.

In another preferred embodiment, the composition further comprises the micronutrients and biochemical substances listed in Table 1.

An advantage of the method and composition of the invention provides for a therapeutic approach to arrhythmias that is an alternative to current therapies. Furthermore, another advantage of the invention is that it satisfies the need for a therapy for arrhythmia that is without the side effects generally associated with the other conventional therapies.

BRIEF DESCRIPTION OF THE DRAWINGS

FIG. 1 shows the distribution of Episode Frequency of irregular heartbeat for patients taking vitamin therapy versus the placebo group.

FIG. 2 shows average arrhythmia episode frequency for the vitamin therapy and placebo groups.

DETAILED DESCRIPTION

The electrical impulse for the heart beat is created in specific muscle cells of the heart (myocytes). This type of muscle cell is not susceptible to conscious control as opposed for example to the muscles of the arms or the legs. The biological energy in each cell, including myocytes, is created in the mitochondria of the cell. The most important carriers of biological energy and cofactors of myocyte energy metabolism are certain vitamins, minerals and specific amino acids, such as L-carnitine. They are required as coenzymes in the Krebs-cycle, the respiration chain and for other cellular metabolic functions. L-carnitine is also involved in energy metabolism as a carrier of medium-chain fatty acids across the walls of the mitochondria. The medium-chain fatty acids are then broken down to Acyl groups as part of the cells internal energy or fuel production process. Furthermore, the role of Vitamin C as an important electron transfer molecules and power reducing agent in the body is well known. The conversion of NADP and FADP to NADPH and FADPH is conducted by Vitamin C. Thus, without being bound to a specific mechanism of operation, it is the conception of the instant inventors that proper metabolic function of myocytes with a selection of specific micronutrients is key to preventing and correcting both ventricular as well as atrial arrhythmias. It is believed that the administration of these specific micronutrients generates a sufficient amount of internal cell energy to reduce the occurrence of arrhythmia.

The present invention is described in further detail with reference to the following clinical study example, with no limitation of the invention implied.

EXAMPLE 1

In order to prove the hypothesis that deficiency in the bio-energy cycle of myocytes is a frequent cause of arrhythmias, a double blind, placebo-controlled clinical multi-center study was conducted. Inclusion criteria were human patients with paroxysmal atrial arrhythmias. The goal of this study was to evaluate, whether the therapy with an ascorbate compound such as Vitamin C (Ascorbic Acid) or its pharmaceutical acceptable ascorbate salts, or a mixture thereof and a carnitine compound such as L-carnitine hydrochloride or other pharmaceutically acceptable L-carnitine salts, or a mixture thereof, can reduce the number of clinically relevant episodes of irregular heartbeats. Some of the more important micronutrients listed in Table 1, in addition to Vitamin C and L-Carnitine, are Coenzyme Q10, taurine and magnesium. The administered biochemical composition preferably includes Coenzyme Q10, taurine and magnesium or their pharmaceutically acceptable taurine salts or their mixtures. In another preferred embodiment, the biochemical composition includes Vitamin B1 and Vitamin B2. It is understood that the specific amounts of biochemical micronutrients (biochemical substances) listed in Table 1 are as part of an example and a general guideline, and specifically that the amounts of Vitamin C, L-Carnitine, Coenzyme Q10, taurine and magnesium, can be adjusted higher or lower in range, or by administration of multiple of daily doses of the same composition to achieve the same results.

The biochemical substances can be co-administered as separate compounds or certain of its compounds can be covalently bound together in the form of a new compound. Furthermore, the biochemical composition may be in the form of tablets, powders, pills, and food stuffs, such as a health bar or cereals. Alternatively, the composition may be given intravenously in the form of injections and infusions, inhalations, suppositories or other pharmaceutically acceptable carriers, for rapid absorption and effect.

TABLE 1

| Biochemical Substances (Micronutrients) | Units | Amount |
|---|---|---|
| Vitamin C | mg | 1300 |
| Vitamin A | I.U. | 1665 |
| Biotin | mcg | 195 |
| Calcium | mg | 48 |
| Chromium Glycinate | mcg | 10 |
| Citrus Bioflavonoids | mg | 100 |
| Coenzyme Q10 | mg | 27 |
| Copper Glycinate | mcg | 330 |
| Vitamin D3 | I.U. | 130 |
| Vitamin E | I.U. | 200 |

TABLE 1-continued

| Biochemical Substances (Micronutrients) | Units | Amount |
|---|---|---|
| d-Calcium Pantothenate | mg | 80 |
| Folic Acid | mcg | 90 |
| Inositol | mg | 35 |
| L-Arginine | mg | 40 |
| L-Carnitine | mg | 195 |
| L-Cysteine | mg | 35 |
| L-Lysine | mg | 110 |
| L-Proline | mg | 110 |
| L-Selenomethionine | mcg | 20 |
| Magnesium Glycinate | mg | 40 |
| Manganese Chelate | mcg | 1300 |
| Molybdenum Glycinate | mcg | 4 |
| Niacin | mg | 75 |
| Vitamin B12 Cyanocobalamin | mcg | 27 |
| Phosphorus | mg | 15 |
| Potassium Proteinate | mg | 20 |
| Pycnogenol | mg | 7 |
| Vitamin B6 Pyridoxine | mg | 14 |
| Vitamin B2 Riboflavin | mg | 22 |
| Taurine | mg | 200 |
| Vitamin B1 Thiamine | mg | 22 |
| Zinc Glycinate | mg | 7 | mg = milligrams,
mcg = micrograms,
I.U. = International Unit

The chemical structure of the substances in Table 1 are well known and are commercially available through a variety of sources.

Study Design:

120 human patients with irregular heartbeat were randomly divided into 2 groups. One group received a defined program of micronutrients for oral consumption and the second group received placebos. The length of the study was 6 months.

Study Results:

The administration of the biochemical substances results in a decrease of the clinically relevant episodes of irregular heartbeat, without any indication of side effects.

Fewer patients in the placebo therapy group exhibited 10 or less occurrences of arrhythmia than those patients in the vitamin group. The opposite is true with patients in the higher frequency of arrhythmia, where less patients in the vitamin group exhibited more than 10 episodes of arrhythmia within the 6 month period of study than in the placebo group. The difference between the two groups was statistically significant.

The average frequency of irregular heartbeat in the group with vitamin therapy is with 25.2 episodes per patient and the average frequency for the placebo group was 42.4%. Thus, the average frequency for irregular heart beat was approximately 41% lower in the vitamin therapy group. Thus, the intake of essential biochemical composition so described is an effective and safe alternative to conventional drugs in the treatment of arrhythmia.

Thus, the intake of essential biochemical composition so described is an effective and safe alternative to conventional drugs in the prevention and treatment of arrhythmia.

Thus, the invention provides for a specific therapeutic approach to arrhythmias that is an alternative to current therapies. Furthermore, the invention satisfies the need for a therapy for arrhythmia that is without the side effects generally associated with the conventional therapies currently available.

The invention claimed is:

1. A method of treatment of arrhythmia in the cardiac muscle of a human host in need thereof, the method comprising: administering to said host an effective amount of a composition of the following biochemical substances: Vitamin C, Vitamin A, Biotin, Calcium, Chromium Glycinate, Citrus Bioflavonoids, Coenzyme Q10, Copper Glycinate, Vitamin D3, Vitamin E, d-calcium Pantothenate, Folic Acid, Inositol, L-Arginine, L-Carnitine, L-Cysteine, L-Lysine, L-Proline, L-Selenomethionine, Magnesium Glycinate, Manganese Chelate, Molybdenum Glycinate, Niacin, Vitamin B12 Cyanocobalamin, Phosphorus, Potassium Proteinate, Pycnogenol, Vitamin B6 Pyridoxine, Vitamin B2 Riboflavin, Taurine, Vitamin B1 Thiamine, and Zinc Glycinate; and thereby ameliorating said arrhythmia.

2. The method of claim 1 wherein the taurine compound is selected from the group consisting of taurine hydrochloride, and pharmaceutically acceptable taurine salts.

3. The method of claim 1 wherein the composition is administered to the human host
   a) orally in the form of tablets, powders, pills, and food stuffs.

4. A method of treatment of arrhythmia in the cardiac muscle of a human host in need thereof, the method comprising: administering to said host an effective amount of a composition of biochemical substances comprising: Vitamin C 1300 mg, Vitamin A 1665 I.U., Biotin 195 mcg, Calcium 48 mg, Chromium Glycinate 10 mcg, Citrus Bioflavonoids 100 mg, Coenzyme Q10 27 mg, Copper Glycinate 330 mcg, Vitamin D3 130 I.U., Vitamin E 200 I.U., d-calcium Pantothenate 80 mg, Folic Acid 90 mcg, Inositol 35 mg, L-Arginine 40 mg, L-Carnitine 195 mg, L-Cysteine 35 mg, L-Lysine 100 mg, L-Proline 110 mg, L-Selenomethionine 20 mcg, Magnesium Glycinate 40 mg, Manganese Chelate 1300 mcg, Molybdenum Glycinate 4 mcg, Niacin 75 mg, Vitamin B12 Cyanocobalamin 27 mcg, Phosphorus 15 mg, Potassium Proteinate 20 mg, Pycnogenol 7 mg, Vitamin B6 Pyridoxine 14 mg, Vitamin B2 Riboflavin 22 mg, Taurine 200 mg, Vitamin B1 Thiamine 22 mg, and Zinc Glycinate 7 mg; and thereby ameliorating said arrhythmia.

* * * * *